United States Patent [19]

Lempert et al.

[11] Patent Number: 4,587,049

[45] Date of Patent: May 6, 1986

[54] AZETIDINONE ACETIC ACID DERIVATIVES AND PROCESS FOR THE PREPARATION THEREOF

[75] Inventors: Károly Lempert; Ferenc Bartha; Gábor Doleschall; József Fetter; Gyula Hornyák; József Nyitrai; Gyula Siming, all of Budapest; Károly Zauer, Szentendre, all of Hungary

[73] Assignees: Richter Gedeon Vegyeszeti Gyar RT, Budapest; Byogal Gyogyszergyar, Debrecen, both of Hungary

[21] Appl. No.: 549,681

[22] Filed: Nov. 7, 1983

[30] Foreign Application Priority Data

Nov. 5, 1982 [HU] Hungary ............... 3560/82

[51] Int. Cl.⁴ .................................. C07D 205/08
[52] U.S. Cl. .................. 260/239 A; 560/37; 560/43; 560/39; 560/41; 260/239 AA
[58] Field of Search ................ 260/239 AL

[56] References Cited

U.S. PATENT DOCUMENTS 4,290,947  9/1981  Christensen et al. .......... 260/239 A
4,435,322  3/1984  Lempert et al. ............... 260/239 A

OTHER PUBLICATIONS

Sumitomo et al, Chem. Abs., 101, 72518b (1983).

*Primary Examiner*—Mark L. Berch
*Attorney, Agent, or Firm*—Karl F. Ross; Herbert Dubno

[57] ABSTRACT

The invention relates to compounds of the general formula (X)

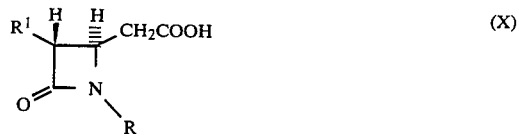

wherein

R is as a removable protecting substituent of the amido group a phenyl group or a benzyl group substituted by one or more alkoxy group(s) having 1–4 carbon atoms and $R^1$ stands for a hydrogen atom or an alkyl group having 1–4 carbon atoms and a process for the preparation thereof.

The compounds of the general formula (X) can be prepared from the starting materials of the general formula (V), wherein R and $R^1$ are as stated above and Z is an alkyl group having 1–4 carbon atoms.

The compounds of the general formula (X) are useful pharmaceutical intermediates which can be used in the preparation of known antibiotics (e.g. Thienamycin and PS-5).

5 Claims, No Drawings

AZETIDINONE ACETIC ACID DERIVATIVES AND PROCESS FOR THE PREPARATION THEREOF

FIELD OF THE INVENTION

This invention relates to new heterocyclic acetic acid derivatives and a process for the preparation thereof.

According to a feature of the present invention there is provided a process for the preparation of new compounds of the formula (X), (X)

wherein
R is as a removable protecting substituent of the amido group, a phenyl group or a benzyl group substituted by one or more alkoxy group(s) having 1-4 carbon atoms and
$R^1$ stands for a hydrogen atom or an alkyl group having 1-4 carbon atoms.

BACKGROUND OF THE INVENTION

The above new compounds are racemic intermediates of thienamycin and other compounds of similar structure. The preparation of thienamycin and PS-5 from the compounds of the formula (X) is shown on the next page.

1. Ph$_2$CHN$_2$
2. K$_2$S$_2$O$_8$

H$_2$/Pd/C

J. Chem. Soc. Perkin I 2228 (1981)

(±) Ps-5

1. K$_2$S$_2$O$_8$
2. NaBH$_4$

DE-OS 2751 597

(±) Thienamycin

Thienamycin is an antibiotic of broad spectrum. The microbiological preparation of this antibiotic is disclosed in U.S. Pat. No. 3,950,357 and the synthesis thereof in Published German Patent Specification No. 2,751,597.

The first step of the above synthesis has a yield below 10% and therefore the process is very uneconomic.

The microbiological preparation of PS-5 having similar effect and of related compounds is described in Japanese Patent Specification No. 5 4151-598 and the synthesis thereof is reported by Kametani et al. [J. Chem. Soc. Perkin I. 2228 (1981)]; the yields, however, are low.

DESCRIPTION OF THE INVENTION

It has been found that thienamycin and PS-5 intermediates of the formula (X) can be prepared from the starting materials of the formula (V) in a more simple manner than by the known methods. According to an alternative process the compounds of the formula (X) can also be prepared from the compounds of the formula (VIII).

(V)   (VIII)

The compounds of the formulae (V) and (VIII), in which $R^1$ is hydrogen, are protected in a separate patent application, but the preparation thereof is illustrated in the present specification by Examples.

The starting materials of the formula (V), in which $R^1$ is an alkyl group having 1-4 carbon atoms, and the compounds of the formula (IV)

(IV)

are disclosed the first time in the present specification. In the said formulae R and $R^1$ are as stated in connection with the formula (X) and Z stands for an alkyl group having 1-4 carbon atoms. The preparation of the new starting materials is disclosed in the body of the specification and the Examples, respectively.

According to the present invention there is provided a process for the preparation of new compounds of the formula (X)
wherein
R is a removable protecting substituent of the amido group in the form of a phenyl group or a benzyl group substituted by one or more alkoxy groups having 1-4 carbon atoms and
$R^1$ is hydrogen or an alkyl group having 1-4 carbon atoms which comprises
(a$_1$) hydrolyzing a compound of the formula (V)

(V)

or an isomeric mixture thereof wherein Z is C$_{1-4}$ alkyl to yield a compound of the formula (VI), (VI)

—activating said compound on the carboxy group-
—and then reacting with diazomethane to yield a compound of the formula (VII)

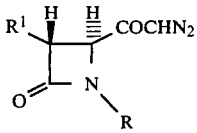

optionally together with the methyl ester of a compound of the formula (VI), subjecting said compounds to diazo-exchange in the presence of water in a manner known per se and isolating the compound of the formula (X); or ($a_2$) activating a compound of the formula (VI) on the carboxy group and then reacting it with diazomethane to yield a compound of the formula (VII) optionally together with the methyl ester of a compound of the formula (VI), subjecting said compounds to diazo-exchange in the presence of water in a manner known per se and isolating the compound of the formula (X); or ($a_3$) subjecting a compound of the formula (VII) optionally comprising the methyl ester of a compound of the formula (VI) to diazo-exchange in the presence of water in a manner known per se and isolating the compound of the formula (X); or ($b_1$) subjecting a compound of the formula (VII), wherein R and $R^1$ are as stated above, to diazo-exchange in the presence of an alkanol having 1–4 carbon atoms in a manner known per se and hydrolyzing the compound of the formula (IX)

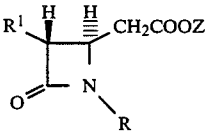

so obtained wherein R and $R^1$ are as stated above and Z is an alkyl group having 1–4 carbon atoms to yield a compound of the formula (X); or ($b_2$) hydrolyzing a compound of the formula (IX) and isolating the compound of the formula (X) so obtained; or (c) reacting a compound of the formula (VIII)

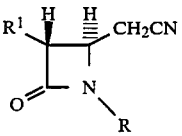

(wherein R and $R^1$ are as stated above) with an alkanol having 1–4 carbon atoms and hydrogen chloride gas and hydrolyzing the compound of the formula (IX) so obtained to yield a compound of the formula (X).

According to process variant (a) the compound of the formula (V) or an isomeric mixture thereof is used as starting material. The said starting materials can be prepared as follows:

In the first step a dialkyl-[(substituted amino)-malonate] of the formula (I)

R—NHCH(COOZ)$_2$ (I)

(wherein R and Z are as stated above) is reacted with an acylating agent of the formula (II)

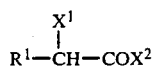

wherein $X^1$ and $X^2$ are the same or different and stand for halogen. The compound of the formula (III)

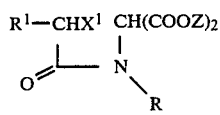

thus obtained is subjected to cyclization in the presence of an acid binding agent—preferably a tertiary amine—to yield a compound of the formula (IV).

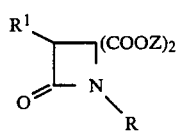

The compound of the formula (IV) is reacted with an alkali metal halide (preferably sodium or lithium chloride) in the presence of pyridine, quinoline or a homologue thereof or a mixture of the said amines or in the simultaneous presence of dimethyl sulfoxide and water to yield a compound of the formula (V).

In the case of esters of the formula (V), wherein $R^1$ is hydrogen, one compound is formed, while in the case of compounds of the formula (V), wherein $R^1$ is alkyl having 1–4 carbon atoms, the mixture of the cis and trans isomers is obtained.

In the latter case the isomer mixture is either separated and the trans isomer is converted into the corresponding acid of the formula (VI) or the isomer mixture is used as starting material of method (a).

The mixture of the isomers of the formula (V) can optionally be separated by chromatography. As adsorbent Kieselgel 60 (diameter 0.063–0.2000 mm) can be used and as eluant benzene, thereafter mixtures of benzene and acetone are applied in which the ratio of acetone is gradually increased up to 9:1 benzene-acetone ratio.

In the first step of method (a) the compounds of the formula (V) thus obtained are subjected to alkaline hydrolysis. The alkali can be used in equimolar amount or in a reasonable excess.

If an isomeric mixture of a compound of the formula (V), in which $R^1$ is an alkyl group having 1–4 carbon atoms, is used as starting material, the hydrolysis of the trans ester takes place completely and rapidly while the cis ester hydrolyzes partially and slowly. Thus, the trans carboxylic acid of the formula (VI) is obtained as the main product which contains some cis carboxylic acid and the cis component of the unreacted isomer mixture of the formula (V). From the reaction mixture only the trans carboxylic acid of the formula (IV) precipitates in crystalline form.

The trans carboxylic acid of the formula (VI) can be prepared from the compounds of the formula (IV) without isolating the intermediate of the formula (V) as well.

In the second step of method (a) at first the carboxy group of the azetidinone carboxylic acid of the formula (VI) is activated. This can be carried out with the aid of any activator of the carboxy group which is compatible with the β-lactam ring. It is preferred to form a mixed anhydride, advantageously with ethyl chloroformiate. The formation of the mixed anhydride is accomplished in the presence of a tertiary amine. The salt of the tertiary amine precipitates from the reaction mixture and is removed.

The compound of the formula (VI) activated on the carboxy group is then reacted with diazomethane. The diazomethane can be prepared from any suitable compounds (e.g. N-methyl-N-nitroso urea or N-methyl-N-nitroso-p-toluene-sulfonamide). It is preferred to add the diazomethane in form of an etheral solution. When the development of gas has ceased the excess of diazomethane is preferably decomposed with acetic acid and the compound of the formula (VII) thus obtained is isolated and if necessary purified (e.g. by column chromatography).

The compound of the formula (VII) thus obtained may contain as by-product the methyl ester of the trans carboxylic acid of the formula (VI). The presence of this compound does not affect, however, the next reaction step in an adverse manner so the removal thereof is not necessary.

The compound of the formula (VI) thus obtained, which can optionally contain the methyl ester of the acid of the formula (VI), is subjected to a Wolff re-arrangement known per se in the fourth step of method (a) whereupon the α-diazoketone side-chain converts first into a ketene by nitrogen elimination and then it reacts with water to yield an azetidinone acetic acid of the formula (X).

The Wolff re-arrangement can be carried out by irradiation with ultraviolet light in the presence of a catalyst or by thermal treatment or combination of the said two methods. One may proceed preferably by using irradiation with ultraviolet light. Irradiation may be accomplished e.g. in a photoreactor preferably under an inert gas and in the presence of water and optionally an inert organic solvent.

The compound thus obtained may be isolated from the reaction mixture by evaporation and/or phase exchange methods and can be purified by recrystallization, if necessary.

According to method (b) a compound of the formula (VII), which may optionally contain the methyl ester of the corresponding compound of the formula (VI), is subjected to Wolff re-arrangement in the presence of an alkanol having 1-4 carbon atoms and the compound of the formula (IX) thus obtained is hydrolyzed. The hydrolysis is carried out in an alkaline medium.

According to method (c) a compound of the formula (VIII) is used as starting material. The compounds of the formula (VIII) can be prepared from the corresponding compound of the formula (V) as described in Example 2 (Method I, Examples a–d). The compound of the formula (VIII) is reacted with an alkanol having 1-4 carbon toms and hydrogen chloride gas and the compound of the formula (IX) thus obtained is subjected to alkaline hydrolysis to yield a compound of the formula (X).

According to another feature of the present invention there are provided new compounds of the formula (X) wherein R is a benzyl group optionally substituted by one or more alkoxy groups having 1-4 carbon atoms and $R^1$ stands for a hydrogen atom or an alkyl group having 1-4 carbon atoms.

Preferred representatives of the compounds of the formula (X) are the following: [1-(2,4-dimethoxy-benzyl)-4-oxo-2-azetidinyl]-acetic acid; [trans-1-(2,4-dimethoxy-benzyl)-3-ethyl-4-oxo-2-azetidinyl]-acetic acid.

According to a further feature of the present invention there are provided new compounds of the formula (IX) wherein R stands for a benzyl group substituted by one or more alkoxy groups having 1-4 carbon atoms; and $R^1$ is a hydrogen atom or an alkyl group having 1-4 carbon atoms.

A preferred representative of the compounds of the formula (IX) is the ethyl [1-(2,4-dimethoxy-benzyl)-2-azetidinyl]-acetate.

According to a still further feature of the present invention there are provided new compounds of the formula (VII) wherein R stands for a benzyl group substituted by one or more alkoxy groups having 1-4 carbon atoms; and $R^1$ is a hydrogen atom or an alkyl group having 1-4 carbon atoms.

Preferred representatives of the compounds of the formula (VII) are the following derivatives: 4-diazoacetyl-1-(2,4-dimethoxy-benzyl)-2-azetidinone; and trans-4-diazoacetyl-1-(2,4-dimethoxy-benzyl)-3-ethyl-2-azetidinone.

According to a still further feature of the present invention there are provided new compounds of the formula (VI) wherein R stands for a benzyl group substituted by one or more alkoxy groups having 1-4 carbon atoms; and $R^1$ is a hydrogen atom or an alkyl group having 1-4 carbon atoms.

Preferred representatives of the compounds of the formula (VI) are the following derivatives: trans-1-(2,4-dimethoxy-benzyl)-3-ethyl-4-oxo-2-azetidine-carboxylic acid; and 1-(2,4-dimethoxy-benzyl)-4-oxo-2-azetidine-carboxylic acid.

SPECIFIC EXAMPLES

Further details of the present invention are shown in the following non-limiting Examples.

EXAMPLE 1

Preparation of
[1-(2,4-dimethoxy-benzyl)-4-oxo-2-azetidinyl]-acetic acid 2.0 g (6.94 millimoles) of 4-diazoacetyl-1-(2,4-dimethoxy-benzyl)-2-azetidinone are dissolved in a mixture of 100 ml of peroxide-free tetrahydrofuran and 50 ml of water and the solution is irradiated with a high pressure mercury vapor lamp (HPK 125) under argon in a pyrex apparatus equipped with a submersed lamp for 4 hours. The solution is evaporated to about 50 ml. The residue is diluted with water to 120 ml and made alkaline by adding 2.8 ml of a 10% sodium hydroxide solution. The aqueous solution is extracted three times with 20 ml of dichloromethane each, the aqueous layer is acidified with concentrated hydrochloric acid to pH 2 and re-extracted three times with 20 ml of dichloromethane each. The dichloromethane layer is dried over anhydrous magnesium sulfate, filtered and the filtrate is evaporated to dryness. The brownish-yellow crystalline residue is recrystallized from benzene. Thus 1.63 g of the aimed compound are obtained, yield 84%. M.p.: 112° C.

The starting material can be prepared as follows:

(a) 109.7 g (0.66 mole) of 2.4-dimethoxy-benzaldehyde and 72 ml (0.66 mole) of benzyl amine are stirred in 660 ml of methanol at room temperature for 20 minutes (at the beginning a suspension is formed which turns into a clear solution) whereupon 13.2 g (0.33 mole) of sodium-[tetrahydro-borate(III)] are added in small portions under external cooling with ice-cold water.

The reaction is followed by thin layer chromatography (layer: Kieselgel G; according to Stahl; developing agent: benzene-acetone 9:1). The reaction having been completed the mixture is evaporated to dryness in vacuo, to the residue 300 ml of water are added and the mixture is extracted with 500 ml of ether. The aqueous layer is extracted twice with 200 ml of ether each. The united etheral phases are dried over magnesium sulfate, filtered and to the filtrate 112 ml (0.66 mole) of diethyl-bromomalonate and 93 ml (0.66 mole) of triethylamine are added. The reaction mixture is stirred at room temperature for 2–3 days. The precipitated triethyl ammonium bromide is filtered off and washed with ether. The mother liquor is vaporated and the residue crystallized from 150 ml of ethanol. Thus 210 g of a crude product are obtained which is recrystallized from 400 ml of ethanol. Thus 197 g of diethyl(N-benzyl-N-(2,4-dimethoxy-benzyl)-amino-malonate are obtained, yield: 72%. M.p.: 62°–63° C. (from ethanol). IR(KBr): 1750/1725 cm$^{-1}$, d.

(b) 61,7 g (0.149 mole) of diethyl(N-benzyl)-N-(2,4-dimethoxy-benzyl)-amino-malonate prepared according to the preceding paragraph are hydrogenated in 500 ml of methanol in the presence of about 20 g of palladium charcoal catalyst under atmospheric pressure. The catalyst is filtered off and the filtrate evaporated. Thus 47.1 g of diethyl N-(2.4-dimethoxy-benzyl)-amino-malonate are obtained, yield: 97%. The product can be converted into an acid addition salt formed with hydrochloric acid, if desired. The hydrochloride melts at 122°–124° C. (ethyl acetate).

Elementary analysis: for the formula $C_{16}H_{24}ClNO_6$ (361,82) calculated, %: C 53.11; H 6.69; Cl 9.80; N 3.87; found, %: C 52.51; H 6.77; Cl 10.30; N 4.09.

IR (film): 3250, 2900, 2850, 1730, 1720 cm$^{-1}$.

$^1$H-NMR (CDCl$_3$): δ1.3 (t, 6H); 3.78 (s, 3H); 3.82 (s, 3H); 4.21 (q, 4H); 6.20 (s, 2H); 6.4–6.6 (m, 2H)+7.3–7.55 (m, 1H); 7.7 (br, s, 1H).

(c) A mixture of 47 g (0,144 mole) of diethyl-[N-(2,4-dimethoxy-benzyl)-amino-malonate] prepared according to the preceding paragraph, 13.8 ml (19.6 g, 0.173 mole) of chloroacetylchloride and 200 ml of anhydrous benzene are heated to boiling for 3.5 hours. The benzene is distilled off, the residual oil is recrystallized from about 100 ml of ethanol. Thus diethyl N-(2,4-dimethoxy-benzyl)-N-(chloroacetyl)-amino-malonate is obtained with a yield of 66%. M.p.: 83°–84° C.

Elementary analysis: for the formula $C_{18}H_{24}ClNO_7$ (401.84) calculated, %: C 53.80; H 6.02; Cl 8.82; N 3.49; found, %: C 53.63; H 6.26; Cl 8.79; N 3.56.

IR (KBr): 2920; 1755, 1680 cm$^{-1}$.

$^1$H-NMR (CDCl$_3$): δ1.2 t (6H); 3.72 s (6H); 4.08 q (4H); 4.17 s (2H); 4.56 s (2H); 4.95 s (1H); 6.2–6.6 m (2H)+6.95–7.25 m (1H).

(d) A mixture of 35 g (0.087 mole) of diethyl-[N-(2,4-dimethoxy-benzyl)-N-(chloro-acetyl)-amino-malonate], 15.9 ml (11.4 g, 0.113 mole) of triethylamine and 200 ml of anhydrous benzene is heated to boiling for 8 hours. The mixture is extracted successively with 100 ml of water, 100 ml of diluted hydrochloric acid and 100 ml of water, the benzene phase is dried over anhydrous magnesium sulfate, filtered and the filtrate is evaporated. Thus 28,4 g of diethyl-[1-(2,4-dimethoxy-benzyl)-4-oxo-2,2-azetidine-dicarboxylate] are obtained, yield: 89%. B.p.: 175°–180° C./0.1 Hgmm.

Elementary analysis: for the formula $C_{18}H_{23}NO_7$ (365,38) calculated, %: C 59.17; H 6.34; N 3.83; found, %: C 59.24; H 6.24; N 3.54.

IR (KBr): 2900; 1760–1720 cm$^{-1}$.

$^1$H-NMR (CDCl$_3$): δ1.15 t (3H); 1.25 t (3H); 3.25 s (2H); 3.7 s (6H); 3.8–4.25 m (4H); 34.50 s (2H); 6.3 m (2H)+7.0 d (1H).

(e) A mixture of 66.2 g (0.18 mole) of diethyl[1-(2,4-dimethoxy-benzyl)-4-oxo-2,2-azetidine-dicarboxylate] prepared according to the preceding paragraph, 70 ml of dimethyl sulfoxide, 12.7 g (0.22 mole) of sodium chloride and 6.5 ml (0.36 mole) of water is stirred on an oil bath (temperature 170°–180° C. for 6 hours. The reaction mixture is poured into 500 ml of a saturated aqueous sodium chloride solution, extracted five times with 100 ml ethyl acetate each, the organic phase is dried over anhydrous magnesium sulfate, filtered and from the filtrate the ethyl acetate is distilled off. Thus 47.6 g of ethyl-[1-(2,4-dimethoxy-benzyl)-4-oxo-2-azetidine-carboxylate] are obtained. B.p.: 170°–176° C./0.15 Hgmm.

Elementary analysis for the formula $C_{15}H_{19}NO_5$ (293,32) calculated, %: C 61.42; H 6.53; N 4.77; found, %: C 61.25; H 6.87; N 4.58.

IR (film): 2900; 1750–1725 cm$^{-1}$.

(f) To a solution of 5.80 g (0.020 mole) of ethyl-[1-(2,4-dimethoxy-benzyl)-4-oxo-2-azetidine-carboxylate] in 25 ml of ethanol a solution of 0.88 g (0.022 mole) of sodium hydroxide and 60 ml of water is added. The reaction solution is stirred for 2 hours and extracted three times with 20 ml of ether each. The aqueous layer is acidified to pH 2 with concentrated aqueous hydrochloric acid and extracted three times with 20 ml of dichloromethane each. The united organic solutions are dried over anhydrous magnesium sulfate, filtered and from the filtrate the dichloromethane is distilled off. The residue is treated with ether, the yellowish-white crystalline product is filtered off and recrystallized from benzene. Thus 4.0 g of 1-(2,4-dimethoxy-benzyl)-4-oxo-2-azetidine-carboxylic acid are obtained. Yield: 75.4%. M.p.: 124°–125° C.

Elementary analysis: for the formula $C_{13}H_{15}NO_5$ (265.26). calculated, %: C 58.86; H 5.70; N 5.28; found, %: C 58.83; H 5.93; N 5.49.

IR(KBR): 3500–2300, 1735, 1695 cm$^{-1}$.

(g) 13.2 g (50 millimoles) of 1-(2,4-dimethoxy-benzyl)-4-oxo-2-azetidine-carboxylic acid prepared according to the preceding paragraph are dissolved in 150 ml of anhydrous tetrahydrofurane and to the solution first 7.3 ml (52.5 millimole) of triethylamine and thereafter under stirring and ice-cooling 5.0 ml (52.5 millimoles) of ethylchloroformiate are added. The mixture is cooled to −15° C., stirred at this temperature for 20 minutes and the precipitated triethylamine salt is filtered off under argon. To the filtrate a solution of 22.5 g (150 millimole) diazomethane and 230 ml of cold diethyl ether is added. The solution is stirred, allowed to warm to ambient temperature and after 2 hours the mixture is evaporated to dryness. The residue is dissolved in 20 ml of benzene and subjected to column chromatography (adsorbent: 150 g of Kieselgel G, diameter 0.063–0.2000 mm; eluant: benzene-acetone 7:2). On rubbing with ether a crystalline product is obtained. Yield: 10.5 g (73%) of 4-diazoacetyl-1-(2,4-dimethoxy-benzyl)-2-azetidinone, m.p.: 90°–91° C.

Elementary analysis: for the formula $C_{14}H_{15}N_3O_4$ (289.28) calculated, %: C 58.12; H 5.23; N 14.52; found, %: C 58.24; H 5.45; N IR(KBr): 2100, 1740, 1625 cm$^{-1}$.

EXAMPLE 2

Preparation of [1-(2,4-dimethoxy-benzyl)-4-oxo-2-azetidinyl]-acetic acid

To a solution of 0.31 g (1 millimole) of ethyl [1-(2,4-dimethoxy-benzyl)-4-oxo-2-azetidinyl]-acetate and 4 ml of ethanol a solution of 0.04 g (1 millimole) of sodium hydroxide and 6 ml of water are added. The reaction mixture is stirred at room temperature for 2 hours. The solution is extracted three times with 3 ml of dichloromethane each. The aqueous layer is acidified with concentrated aqueous hydrochloric acid to pH 2 and extracted three times with 3 ml of dichloromethane each. The united organic layers are dried over anhydrous magnesium sulfate, filtered and the filtrate is evaporated. The residue is crystallized from benzene. Thus 0.27 g of the desired compound are obtained, yield: 88%, M.p.: 112° C.

Elementary analysis: for the formula $C_{14}H_{17}NO_5$ (279.29) calculated, %: C 60.20; H, 6.13; N 5.02; found, %: C 60.45; H 6.34; N 4.96.

IR(KBr): 3500–2300, 1740, 1690 cm$^{-1}$.

The starting material can be prepared according to the following methods:

Method I (a) 47.6 g (0.162 mole) of ethyl 1-(2,4-dimethoxybenzyl)-4-oxo-2-azetidine-carboxylate prepared according to paragraph e) of Example 1 are reacted with 12.4 g (0.327 moles) of sodium-[tetrahydro-borate(III)] in 200 ml of methanol under external ice-cooling. The reaction takes place within about half an hour. The solution is made neutral by adding diluted hydrochloric acid, the methanol is distilled off and the oil precipitated from the aqueous mixture is extracted five times with 50 ml of ethyl acetate each. The united ethyl acetate layers are dried over anhydrous magnesium sulfate, filtered and the filtrate is evaporated. Thus 39.1 g of 1-(2,4-dimethoxy-benzyl)-4-(hydroxymethyl)-2-azetidinone are obtained. Yield: 96%.

IR (film): 3350; 2900; 1750–1700 cm$^{-1}$.

$^1$H-NMR (CDCl$_3$): δ2.1 b, s (1H); 2.85 m (2H); 3.65 m (2H); 3.82 s (3H); 3.85 s (3H); 4.05 m (1H); 6.38 s (2H); 6.55 m (2H)+7.25 d (1H).

(b) To a solution of 39.1 g of 1-(2,4-dimethoxy-benzyl)-4-hydroxy-methyl)-2-azetidinone prepared according to the preceding paragraph and 100 ml of pyrridine 15.3 ml (23.6 g, 0.206 mole) of mesyl chloride are added dropwise under external ice-cooling. The reaction mixture is stirred until all the starting material is converted (about 2–3 hours). The mixture is poured onto 500 ml of water. The precipitated oil becomes slowly crystalline. Thus 37.5 g of 1-(2,4-dimethoxy-benzyl)-4-(mesyloxymethyl)-2-azetidinone are obtained. Yield: 73%. M.p.: 71°–72° C. (ether).

Elementary analysis: for the formula $C_{14}H_{19}NO_6S$ (329.36) calculated, %: C 51.05; H 5.81; N 4.25; S 9.74; found, %: C 51.19; H 6.07; N 4.19; S 9.93.

IR(KBr): 1735 cm$^{-1}$.

(c) A mixture of 37.5 g (0.107 mole) of 1-(2,4-dimethoxy-benzyl)-4-(mesyloxymethyl)-2-azetidinone prepared according to the preceding paragraph, 250 ml of anhydrous acetone, and 56.3 g (0.376 mole) of sodium iodide is heated to boiling for 8 hours. To the mixture a further amount of 18.8 g (0.125 mole) of sodium iodide are added and the mixture is stirred for a further 8 hours under boiling. The mixture is evaporated to dryness on a water-bath (internal temperature 50° C.), the residue is rubbed with 100 ml of water and the oil thus obtained is extracted with 100 ml of dichloromethane. The aqueous layer is extracted three times with 50 ml of dichloromethane each. The united dichloromethane layers are dried over anhydrous magnesium sulfate, filtered and the filtrate is evaporated. Thus 40.3 g of 1-(2,4-dimethoxy-benzyl)-4-(iodomethyl)-2-azetidinone are obtained. Yield: 98%.

IR (film): 2920, 1750 cm$^{-1}$.

(d) A solution of 1.2 g (3.3 millimoles) of 1-(2,4-dimethoxy-benzyl)-4-iodomethyl-2-azetidinone and 5 ml of dimethyl formamide is stirred with 0.35 g (7 millimoles) of sodium cyanide at room temperature for 48 hours. The solution is poured onto 30 ml of water and extracted five times with 20 ml of ether each. The etheral solution is dried over anhydrous magnesium sulfate, filtered and the filtrate is evaporated in vacuo. Thus 0.6 g of 4-cyanomethyl-1-(2,4-dimethoxy-benzyl)-2-azetidinone are obtained. Yield: 70%.

Elementary analysis: for the formula $C_{14}H_{16}N_2O_3$ (260.3) calculated, %: N 10.76; found, %: N 10.71.

IR (film): 2920; 2270; 1750 cm$^{-1}$.

(e) To a solution of 5.2 g (20 millimoles) of 4-cyanomethyl-1-(2,4-dimethoxy-benzyl)-2-azetidinone prepared according to the preceding paragraph in 40 ml of anhydrous ether and 40 ml of anhydrous dichloro methane 1.24 ml (21.2 millimoles) of ethanol are added and into the solution gaseous hydrogen chloride developed from 80 ml of concentrated aqueous hydrochloric acid is introduced under stirring and ice-cooling. The mixture is allowed to stand in a refrigerator overnight, the solution is evaporated to dryness and the residue is dissolved in about 25 ml of water. The pH of the aqueous solution is adjusted to 7 by adding a 10% aqueous sodium hydroxide solution and the solution thus obtained is allowed to stand overnight. The mixture becomes blue and the precipitated white crystals are filtered off. The aqueous filtrate is extracted five times with 10 ml of ether each. The united etheral phases are dried over anhydrous magnesium sulfate, filtered and the filtrate is evaporated. The residual oil (1 g) is separated by means of preparative thin layer chromatography (adsorbent: Kieselgel PF$_{254+366}$; develop agent: n-heptane-acetone 7:3). Thus 0.501 g of ethyl [1-(2,4-dimethoxy-benzyl)-4-oxo-2-azetidinyl]-acetate is obtained. Yield: 8.2%.

Elementary analysis: for the formula $C_{16}H_{21}NO_5$ (307,34) calculated, %: C 62.52; H 6.89; N 4.56; found, %: C 62.45; H 6.79; N 4.43.

IR(KBr): 2900, 1760, 1730 cm$^{-1}$.

$^1$H-NMR(CDCl$_3$): 1.22 t (3, J=7 Hz), 4.08 d (2H, J=7 Hz), 2.05–3.28 m (4H); 3.6––3.9 m (1H), 4.12 d+4.42 d (2H, J$_{AB}$==18 Hz, 6.46 m (2H)+7.12 d (1H, I=9 Hz).

Method II

A solution of 2.02 (7 millimoles) of 4-diazoacetyl-1-(2,4-dimethoxy-benzyl)-2-azetidinone and 150 ml of anhydrous ethanol is irradiated with a high pressure mercury vapor lamp (HPK 125) under argon in a pyrex apparatus equipped with a submersed lamp. Irradiation is continued for 3 hours whereupon the solution is evaporated and the residue dissolved in benzene. The solution is purified by column chromatography (adsorbent: Kieselgel 60, diameter: 0.063–0.2000 mm; eluant: benzene-acetone 7:2).

Thus 1.57 g of ethyl [1-(2,4-dimethoxy-benzyl)-2-azetidinyl]-acetate are obtained, yield: 73%. The physical constants of this product are identical with those of that prepared according to Example 2e).

EXAMPLE 3

Preparation of [trans-1-(2,4-dimethoxy-benzyl)-3-ethyl-4-oxo-2-azetidinyl]-acetic acid 2.93 g (10 millimole) of trans-4-diazoacetyl-1-(2,4-dimethoxy-benzyl)-3-ethyl-2-azetidinone-which may contain some methyl-trans-1-(2,4-dimethoxy-benzyl)-3-ethyl-4-oxo-2-azetidine-carboxylate too—are dissolved in 100 ml of peroxide-free tetrahydrofuran and to the solution 50 ml of water are added. The solution is irradiated with a high pressure mercury vapor lamp (HPK) under argon in a pyrex apparatus equipped with a submersed lamp for about 4 hours (until the diazoacetyl derivative is converted). From the solution the tetrahydrofuran is evaporated in vacuo, the residue is diluted with water to 150 ml and made alkaline by adding 4 ml of a 10% aqueous sodium hydroxide solution. The alkaline solution is extracted three times with 30 ml of dichloromethane each and the aqueous phase is acidified with concentrated hydrochloride acid to pH 2. The acidic solution is extracted three times with 30 ml of dichloro methane each. The organic phase is dried over anhydrous magnesium sulfate, filtered and the filtrate is evaporated to dryness. On rubbing with ether the residue becomes crystalline. Thus 1.44 g of the desired compound are obtained, yield: 47.1%. M.p.: 131° C.

IR(KBr): 3500–2500, 1750, 1710 cm$^{-1}$.

$^1$H-NMR (CDCl$_3$): 0.93 t (3H; I=0.96 Hz); 1.45–1.90 m (2H); 2.60 d (AB, I$_{vic}$=15.7 Hz, I gem=4.6 Hz, and 8.5 Jz, resp.); 2.76–2.90 m (1H); 3.43 ddd (1H, I==8.6 Hz, 4.6 Hz and 2.0 Hz); 3.78 s (6H); 4.09+4.49 (AB, I=14.7 Hz); 6.36–6.53 m (2H); 7.14 d (1H, I=9 Hz); 7.8 s (1H, exchangeable by D$_2$O).

The starting material can be prepared as follows:

(a) 30 g (0.092 mole) of diethyl N-(2,4-dimethoxybenzyl)-amino-malonate prepared according to paragraph (b) of Example 1 are dissolved in a mixture of 90 ml of benzene and 15.6 ml (11.2 g, 0.111 mole) of triethyl amine and thereafter 20.5 g (0.111 mole) of 2-bromo butyric acid chloride are added dropwise under external ice-cooling. The reaction mixture is stirred under cooling for half an hour and thereafter at room temperature for half an hour. The precipitated crystalline substance is filtered off and washed twice with 20 ml of benzene. To the combined benzene mother liquor 31.2 g (22.4 g, 0.222 mole) of triethyl amine are added and the mixture is boiled for 6 hours. The precipitated crystalline substance is cooled and filtered. The mother liquor is extracted successively with 100 ml of water, twice with 100 ml of diluted hydrochloric acid each (a mixture of 90 ml of water and 10 ml of hydrochloric acid) and twice with 100 ml of water each. The organic layer is dried over anhydrous magnesium sulfate, filtered and the filtrate is evaporated. The residual oil is made crystalline by rubbing with petrolether. Thus 31.5 g of diethyl 1-(2,4-dimethoxy-benzyl)-3-ethyl-4-oxo-2,2-azetidinedicarboxylate are obtained. M.p.: 69° C. (from a mixture of benzene and petrolether).

Elementary analysis: for the formula C$_{20}$H$_{27}$NO$_7$ (393.43) calculated, %: C 61.05; H 6.92; N 3.56; found, %: C 61.30; H 7.06; N 3.63.

$^1$H-NMR (CDCl$_3$): δ1.05 (t, 3H, I=7.2 Hz), 1.08 (t, 3H, I=7.2 Hz), 1.22 (t, 3H, I=7.2 Hz), 1.55–1.9 (m, 2H), 3.66 (t, 1H, I==7.8 Hz), 3.76 (s, 6H), 3.93 (q, 2H, I=7.2 Hz, a very small secondary splitting); 4.19 (q, 2H, I=7.2 Hz, secondary splitting: 1.2–1.6 Hz), 4.4+4.60 (ABq, 2H, I=15.4 Hz), 6.35–6.5 (m, 2H), 7.13 (d, 1H, I=10 Hz).

(b) 55.5 g (0.141 mole) of diethyl 1-(2,4-dimethoxybenzyl)-3-ethyl-4-oxo-2,2-azetidine-dicarboxylate prepared according to Example 3a are dissolved in 70 ml of dimethyl sulfoxide whereupon the solution is admixed with a solution of 9.90 g (0.169 mole) of sodium chloride and 5.11 g (0.282 mole) of water and stirred on an oilbath (180° C.) for 8 hours. The mixture is poured into 500 ml of saturated aqueous sodium chloride solution and extracted with 200 ml and twice with 100 ml of ether each. The organic phase is dried over anhydrous magnesium sulfate, clarified with activated charcoal, filtered and the filtrate is evaporated. Thus 40.8 g of a mixture of cis- and trans-ethyl-[1-(2,4-dimethoxybenzyl)-3-ethyl-4-oxo-2-azetidine-carboxylate] are obtained. Yield: 90%. 5.6 g of this mixture are subjected to column chromatography (adsorbent: Kieselgel-60; diameter 0.063–0.2000 mm; eluant: benzene and benzeneacetone 9:1). The following products are successively eluted in the following order: 0.51 g of cis-isozer, 3.9 g of isomeric mixture and 0.42 g of trans-isomer.

Trans-isomer $^1$H-NMR (CDCl$_3$): δ0.96 t (3H, I=7.2 Hz), 1.24 t (3H, I=7.1 Hz), 1.45–2.0 m (2H), 2.97–3.20 m (1H), 3.54 d (1H, I=2.3 Hz), 3.77 s (3H), 3.79 s (3H), 4.13+4.61 ABq (2H, I=14.3 Hz), 4.17 q (2H, I=7.1 Hz), 6.35–6.5 m (2H), 7.12 d (1H, I=9 Hz).

Cis-isomer $^1$H-NMR (CDCl$_3$): δ1.00 t (3H, I=7.2 Hz), 1.28 t (3H, I=7.1 Hz, 1.45–1.90 m (2H), 3.22 dt (1H, J=5.7 and 7.8 Hz), 3.70 s (3H), 3.78 s (3H), 3.97 d (1H, I==5.7 Hz), 4.21 q (2H, I=7.1 Hz), 4.14+4.60 ABq (2H, I=14.4 Hz), 6.35–6.50 m (2H), 7.10 d (1H, I==9 Hz).

40.8 g (0.127 mole) of the above isomeric mixture and 6.10 g (0.153 mole) of sodium hydroxide are dissolved in 30 ml of water and 100 ml of ethanol and the solution is stirred under external ice-cooling for half an hour. To this solution 300 ml of water are added and the mixture is extracted twice with 100 ml of ether each (thus the non-hydrolyzed cis-isomer is removed). The aqueous phase is acidified with concentrated hydrochloric acid to the pH value of 1. The organic phase is dried over anhydrous magnesium sulfate, filtered and the filtrate is evaporated. The residual oil is crystallized by rubbing with ether. Thus 15 g of trans-1-(2,4-dimethoxy-benzyl)-3-ethyl-4-oxo-2-azetidine-carboxylic acid are obtained. Yield: 36%. M.p.: 122°–123° C.

Elementary analysis: for the formula $C_{15}H_{19}NO_5$ (293.31) calculated, %: C 61.42; H 6.53; N 4.78; found, %: C 61.64, H 6.47; N 4.67.

$^1$H-NMR (CDCl$_3$): δ0.96 t (3H, I=7.0 Hz), 1.50–1.95 m (2H), 3.10–3.30 m (1H), 3.62 d (1H, I=2.2 Hz), 3.77 L s (3H), 3.78 s (3H), 4.16+4.67 ABq (2H, I=15 Hz), 6.36–6.52 m (2H), 7.12 d (1H, I=9 Hz), 8.85 s (1H).

(c) To a solution of 14.65 g (50 millimoles) of trans-1-(2,4-dimethoxy-benzyl)-3-ethyl-4-oxo-2-azetidinecarboxylic acid prepared according to the preceding paragraph in 150 ml of anhydrous tetrahydrofurane 7.3 ml (52.5 millimoles) of triethyl amine are added and to the solution under stirring and ice-cooling 5.1 ml (52.5 millimoles) of ethyl-chloro-formiate are added. The mixture is cooled to −15° C., stirred at this temperature for 20 minutes and the precipitated triethyl amine salt is filtered off under argon. To the filtrate a cold solution of 22.5 g (150 millimoles) of diazomethane and 230 ml of ether is added. The solution is allowed to warm to room temperature under stirring and after 2 hours the reaction mixture is evaporated to dryness. The residue is a mixture comprising predominantly trans-4-diazoacetyl-1-(2,4-dimethoxy-benzyl)-3-ethyl-2-azetidinone and some methyl-trans-1-(2,4-dimethoxybenzyl)-3-ethyl-4-oxo-2-azetidine-carboxylate. The mixture thus obtained can be used as starting material in Example 3 directly, without purification. The benzene solution of the evaporation residue can be, however, subjected to column chromatography, if desired. (Adsorbent: Kieselgel 60. diameter 0.063–0.200 mm, eluant: benzene-acetone 7:2). Thus 9.2 g of trans-4-diazoacetyl-1-(2,4-dimethoxy-benzyl)-3-ethyl-2-azetidinone are obtained. Yield: 59%.

IR (film): 2200, 1750, 1650 cm$^{-1}$.

$^1$H-NMR (CDCl$_3$): δ0.95 t (3H, I=7.0 Hz); 1.5–2.0 m (2H); 2.93–3.12 m (1H), 3.52 d (1H, 2I=2.2 Hz), 3.76 s (3H), 3.78 s (3H), 4.14 és 4.60 (2H, AB; I=14.3 Hz), 5.33 s (1H), 6.36–6.52 m (2H), 7.13 d (1H, I=9 Hz).

EXAMPLE 4

Preparation of diethyl 1-(2,4-dimethoxy-benzyl)-3-methyl-4-oxo-2,2-azetidine-dicarboxylate 95 g (0.292 mole) of diethyl N-(2,4-dimethoxy-benzyl)-amino-malonate are dissolved in a mixture of 350 ml of anhydrous diethyl ether and 47.0 ml (33.8 g, 0.336 mole) of triethyl amine and thereafter 70 g (0.409 mole) of 2-bromo-propionic acid chloride are added dropwise under external cooling with dry ice at a rate that the temperature of the reaction mixture should remain between −30° C. and −20° C. The addition having been completed the reaction mixture is allowed to warm to room temperature and the precipitated crystals are filtered off and washed twice with 50 ml of anhydrous ether each. To the united etheral mother liquor 70.0 ml (50.4 g, 0.500 mole) of triethyl amine are added and the mixture is boiled for 6 hours. The precipitated crystalline substance is filtered cold and the mother liquor is extracted successively with 150 ml of water, a mixture of 130 ml of water and 20 ml of concentrated hydrochloric acid and twice with 150 ml of water each. The organic phase is dried over anhydrous magnesium sulfate, dried and the filtrate is evaporated. The residual oil is made crystalline by rubbing with 50 ml of ether. Thus 66 g of the desired compounds are obtained. Yield: 60%. M.p.: 65° C. (from a mixture of ethyl acetate and petrolether).

From the compound thus obtained [trans-1-(2,4-dimethoxy-benzyl)-3-methyl-4-oxo-2-azetidinyl]-acetic acid can be prepared in a manner analogous to that described in Examples 3b, 3c and 3.

What we claim is:

1. A compound of the Formula (IX)

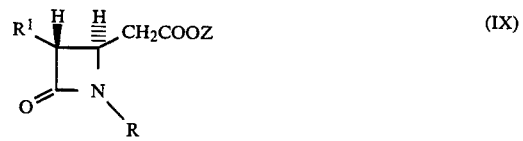

wherein
R is benzyl which can be substituted by one or more alkoxy groups having 1 to 4 carbon atoms;
R$^1$ is hydrogen or alkyl having 1 to 4 carbon atoms; and
Z is C$_1$ to C$_4$ alkyl.

2. Ethyl 1-[(2,4-dimethoxy-benzyl)-4-oxo-2-azetidinyl]-acetate as defined in claim 1.

3. A compound of the formula (X)

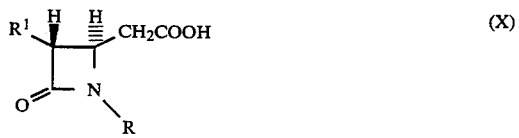

wherein
R is a benzyl group which can be substituted by one or more alkoxy groups having 1 to 4 carbon atoms and R$^1$ is hydrogen or alkyl having 1 to 4 carbon atoms.

4. [1-(2,4-dimethoxy-benzyl)-4-oxo-2-azetidinyl]-acetic acid as defined in claim 3.

5. [Trans-1-(2,4-dimethoxy-benzyl)-3-ethyl-4-oxo-2-azetidinyl]-acetic acid as defined in claim 3.

* * * * *